United States Patent
Al-Zaiti et al.

(10) Patent No.: US 10,820,822 B2
(45) Date of Patent: Nov. 3, 2020

(54) ELECTROCARDIOGRAPHIC IDENTIFICATION OF NON-ST ELEVATION ISCHEMIC EVENTS

(71) Applicant: University of Pittsburgh—Of the Commonwealth System of Higher Education, Pittsburgh, PA (US)

(72) Inventors: Salah Al-Zaiti, Monroeville, PA (US); Ervin Sejdic, Pittsburgh, PA (US); Clifton W. Callaway, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 495 days.

(21) Appl. No.: 15/562,196

(22) PCT Filed: Apr. 12, 2016

(86) PCT No.: PCT/US2016/027105
§ 371 (c)(1),
(2) Date: Sep. 27, 2017

(87) PCT Pub. No.: WO2016/168181
PCT Pub. Date: Oct. 20, 2016

(65) Prior Publication Data
US 2018/0055397 A1 Mar. 1, 2018

Related U.S. Application Data

(60) Provisional application No. 62/146,775, filed on Apr. 13, 2015.

(51) Int. Cl.
*A61B 5/04* (2006.01)
*A61B 5/0472* (2006.01)
(Continued)

(52) U.S. Cl.
CPC ........ *A61B 5/0472* (2013.01); *A61B 5/02007* (2013.01); *A61B 5/04012* (2013.01);
(Continued)

(58) Field of Classification Search
CPC ............ A61B 5/02007; A61B 5/04012; A61B 5/04085; A61B 5/04286; A61B 5/0464;
(Continued)

(56) References Cited

U.S. PATENT DOCUMENTS

| 7,756,572 B1 | 7/2010 | Fard et al. |
| 2007/0208265 A1* | 9/2007 | Couderc .............. A61B 5/0452 600/512 |

(Continued)

OTHER PUBLICATIONS

Arini et al., "Evaluation of ventricular repolarization dispersion during acute myocardial ischemia: spatial and temporal ECG indices," *Med. Biol. Eng. Comput.*, 52:375-391 (Jan. 2014).
(Continued)

*Primary Examiner* — Amanda K Hulbert
(74) *Attorney, Agent, or Firm* — Klarquist Sparkman, LLP

(57) ABSTRACT

Disclosed herein are methods, systems, and devices for identifying increased likelihood of non-ST elevation myocardial infarction (NSTEMI) in a patient based on ECG data. The methods can include determining based on the ECG data that the patient lacks ST elevation (STE) and that the patient exhibits a ventricular repolarization dispersion (VRD) score that exceeds a predetermined threshold value. The VRD score can be based in part on a T wave complexity ratio that serves as a temporal marker of VRD for the patient. Other markers of spatial and time qualities of repolarization can also be included in the VRD score. An elevated VRD
(Continued)

score in the absence of STE can indicate a likelihood of NSTEMI in the patient and a potential major adverse cardiac event.

23 Claims, 8 Drawing Sheets

(51) Int. Cl.
| | |
|---|---|
| *A61B 5/00* | (2006.01) |
| *A61B 5/02* | (2006.01) |
| *A61B 5/0464* | (2006.01) |
| *A61B 5/0468* | (2006.01) |
| *A61B 5/0428* | (2006.01) |
| *A61B 5/0408* | (2006.01) |

(52) U.S. Cl.
CPC .......... *A61B 5/0464* (2013.01); *A61B 5/0468* (2013.01); *A61B 5/04286* (2013.01); *A61B 5/6823* (2013.01); *A61B 5/04085* (2013.01)

(58) Field of Classification Search
CPC ... A61B 5/0468; A61B 5/0472; A61B 5/4836; A61B 5/6823
See application file for complete search history.

(56) References Cited

U.S. PATENT DOCUMENTS

| | | |
|---|---|---|
| 2008/0188762 A1 | 8/2008 | John et al. |
| 2009/0137916 A1 | 5/2009 | Maison-Blanche et al. |
| 2010/0174203 A1 | 7/2010 | Halamek et al. |
| 2014/0257122 A1 | 9/2014 | Ong et al. |

OTHER PUBLICATIONS

International Search Report and Written Opinion for related International Application No. PCT/US2016/027105, dated Jul. 5, 2016, 11 pages.

* cited by examiner

ELECTROCARDIOGRAPHIC IDENTIFICATION OF NON-ST ELEVATION ISCHEMIC EVENTS

CROSS-REFERENCE TO RELATED APPLICATIONS

This is the U.S. National Stage of International Application No. PCT/US2016/027105, filed Apr. 12, 2016, which claims the benefit of U.S. Provisional Patent Application No. 62/146,775, filed Apr. 13, 2015. The provisional application is incorporated by reference herein in its entirety.

FIELD

This disclosure is related to methods, systems, and devices for utilizing electrocardiographic data for identifying non-ST elevation myocardial infarction and other cardiovascular complications.

BACKGROUND

Every year, nearly 7,000,000 Americans present to a hospital with chest pain associated with possible myocardial infarction (MI), which claims nearly one life every two minutes. Reducing ischemic damage associated with MI is a critical step in addressing the issue. The first challenge is the early differentiation of MI patients from others who have similar symptoms but no active coronary events. The second challenge is improving the outcomes of patients with acute MI, given that only a small subset of high-risk patients would benefit from immediate catheterization (e.g., percutaneous coronary intervention [PCI]).

Current methods in this regard are suboptimal because ST elevation (STE) on the prehospital ECG (prevalent in less than 25% of patients with acute MI [STEMI]) remains the principal ECG marker to risk-stratify and guide treatment and destination decisions. The other 75% of MI patients with no-STE (NSTEMI) experience the highest mortality rates with frequently delayed administration of vital treatments (e.g., anti-ischemic, anti-platelet, and anti-coagulant agents). Such treatments are deferred for hours until definitive NSTEMI diagnosis is made based on elevation of serum cardiac enzymes (e.g., troponin). Although point of care devices to measure troponin are readily available, the fact that serum cardiac enzymes are not elevated until only a few hours after the ischemic injury makes their use in the prehospital setting impractical. The standard 10-second, 12-lead ECG remains a good tool for initial patient assessment and treatment decisions, but the absence of markers of ischemic burden in NSTEMI continues to be a challenge.

SUMMARY

More sensitive and specific ECG methods, systems, and devices can lead to a paradigm shift in detecting and intervening in NSTEMI. It has been discovered that novel methods and devices quantifying magnitude of repolarization heterogeneity, ventricular repolarization dispersion (VRD), and/or other properties, can detect myocardial ischemia in the absence of STE. For example, test data shows that a global measure of VRD, without disrupting specificity, can enhance the sensitivity for real-time detection of NSTEMI by about 30% to 50%, improving the selection of high-risk candidates for PCI. As a result, the accurate pre-hospital detection and definitive treatment of NSTEMI can prevent or reduce the size of infarction and greatly improve patient outcomes.

Specific ECG detection of ischemia and/or MI in the absence of STE can improve the speed and accuracy of detecting NSTEMI and selecting proper candidates for immediate revascularization or other treatments. The methods, systems, and devices disclosed herein can detect myocardial ischemia by noting alterations in spatial and temporal indices of VRD. The indices of VRD are dynamic in response to sudden coronary artery occlusion and restoration of normal perfusion in human and animal experiments. The present disclosure describes and compares temporal and spatial repolarization indices in both healthy adults and patients with coronary artery disease.

Test data is presented to demonstrate that myocardial ischemia increases the spatial distribution of the ventricular repolarization process prior to any displacement of the ST segment, which increases spatial VRD, and this distribution can be quantified as distortions of the T waves on the surface 12-lead ECG. Disclosed ECG methods can be used to compute indices of VRD, confirm validity of clinical meaningfulness, and/or determine how to implement patient care. In some embodiments, up to 15 different indices of VRD from patients' ECG data are used to provide a probability score of NSTEMI (e.g., high vs. low probability). Disclosed methods have the potential to save 30,000 or more MI patients each year in the United States alone. Data from nearly 600 chest pain patients have been used to test and develop and validate the disclosed methods, systems, and devices.

Studies described herein confirm validity of clinical meaningfulness of the disclosed technologies (e.g., using VRD to detect NSTEMI). For example, one study (see FIG. 6) was based on chest pain patients (n=47, age 62±12, 60% male) with inconclusive ECGs (i.e., no ST changes) who were referred to exercise testing followed by SPECT scans for ischemia detection. Holter ECG data was recorded during exercise testing and compared the ECG data to SPECT results. Among those with ischemia (n=10), the magnitude of T wave complexity is larger at baseline, increases at the peak of the test, and returns to normal at recovery. Those with no ischemia (controls=37) maintain stable values throughout the test. The tested patients had no ST events during the stress testing. The results of this study support the finding that markers of VRD can serve as useful tools to triage patients.

In another study, a specific index of spatial VRD, the T wave complexity ratio, was used to detect NSTEMI among non-traumatic chest pain patients seen at emergency departments, to quantify the severity of ischemic burden and identify high-risk NSTEMI patients who would benefit from early revascularization (i.e., percutaneous coronary interventions (PCI)), and for other purposes. This testing confirmed that markers of VRD detect myocardial-injury, not merely myocardial ischemia, and hence provide a diagnostic tool for NSTEMI detection. It was shown that, among other things, the T wave complexity ratio increases in patients with NSTEMI relative to other chest pain patients and the absolute values of the T wave complexity ratio are associated with the risk of in-hospital major adverse cardiac events (MACE).

Exemplary methods, systems, and devices for detecting NSTEMI in a patient include determining that the patient lacks STE based on receiving ECG data for the patient and determining the magnitude of VRD (using a T wave complexity ratio and/or other quantitative measures) for the patient based on the ECG data. The technique can include determining a likelihood of NSTEMI, or identifying an increased likelihood of NSTEMI, in a patient who lack of STE where the patient's VRD score is elevated, such as exceeding a predetermined threshold value.

A likelihood of a MACE in the patient can also be based on the determination of a likelihood of NSTEMI in the patient. Once a likelihood of NSTEMI is detected, the patient can be treated for likelihood of MACE.

The T wave complexity ratio has now been found by the present inventors to be a significant factor in detecting NSTEMI in the patient. The T wave complexity ratio is a ratio of a second eigenvalue of repolarization to a first eigenvalue of repolarization. In some methods, the predetermined threshold value for the T wave complexity ratio is at least 0.22 or at least 0.26. Values above the threshold can be used to select patients who have an increased likelihood of NSTEMI.

In disclosed embodiments, the T wave complexity ratio is determined by filtering T waves of the ECG data to derive main principal components analysis (PCA) beats from the ECG data. Deriving main principal components analysis (PCA) beats can comprise reducing the ECG data into three principal beats corresponding to first, second, and third eigenvalues of repolarization.

In some embodiments, the one or more spatial or temporal qualities of VRD comprises T wave complexity (TWC), T loop morphology dispersion (TMD) and/or total cosine R-to-T (TCRT).

In some methods, the ECG data is acquired from the patient when the patient has active ischemia (e.g., angina) but does not have myocardial infarction (MI). The latter is therefore called myocardial injury, rather than myocardial ischemia, and the disclosed studies confirm that markers of VRD are injury-specific, rather than just ischemia-specific. This is essential in disclosed algorithms for detecting NSTEMI and differentiating those patients with actual MI from those with active ischemia but no infarction (e.g., angina), which has important clinical implications in choosing appropriate therapy.

ECG data can be obtained from a patient by applying ECG leads to predetermined positions on the patient's body and detecting ECG signals using an ECG machine or system.

The foregoing and other features and advantages of the disclosed technology will become more apparent from the following detailed description, which proceeds with reference to the accompanying figures.

BRIEF DESCRIPTION OF THE DRAWINGS

FIG. 3A includes a scatter plot and best-fit linear regression mean between peak troponing level at ED and baseline T wave complexity from Holter ECG among NSTEMI cases (n=92). FIG. 3B is an ROC showing point coordinates of T wave complexity to classify NSTEMI events. The vertical line shows an ROC-optimized cutoff point. An area-under-the-curve of 70% suggest that VRD is a good classifier of NSTEMI events, supporting the clinical meaningfulness of the disclosed technology.

DETAILED DESCRIPTION

Figure 1:
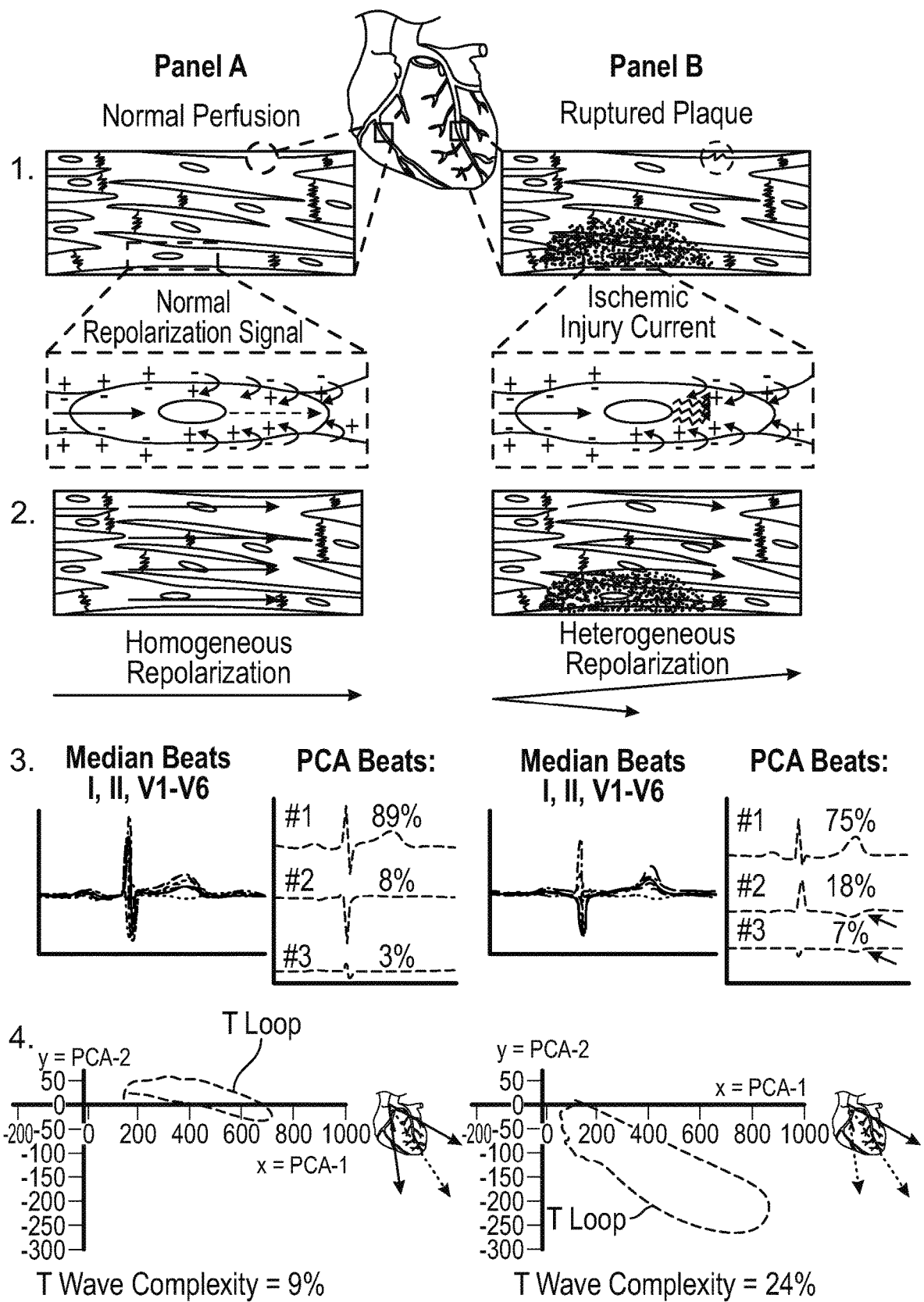
FIG. 1 is an illustration of injury-induced ventricular repolarization dispersion (VRD). The figures in the column labeled Panel A illustrate normal repolarization signal propagation and normal coronary perfusion with corresponding T wave eigenvectors and loop morphology in a 54 year-old male with no coronary events. The figures in the column labeled Panel B illustrate a dispersed repolarization signal and diminished coronary perfusion with corresponding T wave eigenvectors and loop morphology in a 72 year-old female with NSTEMI. The drawings labeled "1" show myocardial tissue. The drawings labeled "2" show a normal repolarization wave and a repolarization wave in response to injury currents. The drawings labeled "3" show principal component analysis (PCA) derived ECG beats. The drawings labeled "4" show plots of T wave amplitude for first PCA beat (x axis) versus second PCA beat (y axis). The ratio between these two PCA eigenvalues is the T wave complexity.

Compared to ST deviation, a simple measure of global ventricular repolarization dispersion (VRD) on the presenting 12-lead ECG can be more sensitive—yet still specific enough—to detect and quantify endo-mid-mural ischemic injury. This can provide a benefit in detecting and risk-stratifying non-ST elevation myocardial infarction (NSTEMI) cases very early. Automated measures of VRD can be easily incorporated in manufacturer-specific devices for real-time display for immediate clinical decision support. This early detection not only has the potential to expedite treatment decisions, but also may reduce unnecessary loss of myocardial tissue in patients with chest pain and no STE.

As described herein, ischemic injury induces VRD, altering the T wave prior to any ST segment deviation. The evaluation of VRD is shown to help detect NSTEMI cases in the emergency department (ED) and elsewhere, and to help identify NSTEMI cases at high risk for in-hospital MACE.

A current ongoing study is taking place at the prehospital division of three hospitals. Consecutive patients with a chief complaint of non-traumatic chest pain or other atypical, suspicious symptoms requiring ECG evaluation were included in this study (current n~600). On the scene, EMS personnel routinely assess the cardiac rhythms and obtain 12-lead ECGs in all chest pain cases as part of standard medical care. We collected these prehospital ECGs and have created a method for determining, in real-time, the probability of NSTEMI using up to 15 markers of VRD. After completion of patient care and medical documentation by the EMS providers, the following protocol was followed:

(1) Subjects meeting the study criteria were identified using custom reporting software in the prehospital electronic patient care record program. Data regarding age, sex, date/time of dispatch, and responding EMS agency were documented for each case as a linkage-list. The prehospital medical records of eligible subjects were made available through an existing hospital-based login for an EMS charts program.

(2) The raw XML files of digital ECGs obtained by monitors used on the scene during the course of the study were stored de-identified on a server such that they could be accessed through the same hospital-based login. These XML files included age/sex, date/time, and were EMS agency stamped and, therefore, were matchable with the prehospital records in the EMS chart program. Linked records were assigned a study ID and forwarded for storage.

(3) The investigators and their research staff abstract data from the EMS records and digital ECG data files for eligible patient cases. Necessary patient identifiers were abstracted and kept separate from the data. For example, EMS's patient encounter reports may have been reviewed to abstract clinical presentation, and prehospital interventions may have been performed.

(4) The investigators and their research staff were then able to use patient identifiers to link prehospital data with inhospital data to abstract necessary medical records for that hospital admission (including, e.g., presenting ECG at the ED). For example, cardiac angiogram summary reports were reviewable to abstract location of culprit artery and severity of occlusion. Hospital records were accessed through a hospital-based login uniquely designed for researchers.

(5) Data was then collected in a de-identified format with only a linkage number for identification of patient cases. Only the minimum necessary protected health information was collected from the prehospital record for inclusion in the linkage list (e.g., name, date of birth, and social security number). This information was sufficient to identify inhospital records for data abstraction. Using these methods, an initial de-identified group of 600 patients (out of a target of 1,438) was recruited.

Electrocardiographic Methods

The 12-lead ECGs can be annotated and interpreted in the following manner:

(1) The digital ECG files are binary XML signals, and a MatLab code (e.g., Sierra code) can convert this signal into common data format (e.g., xls) in which the ECG leads are decoded and stored in columnar matrices (e.g., 12 [leads]× 500 [samples]). Using the raw data, retrieve a 10-second rhythm strip for each lead can be retrieved.

(2) Then, using a singular value decomposition technique, a median beat for each lead can be easily generated. This technique provides high signal-to-noise ratio and yields stable, artifact-free median beats, which controls for baseline noise and artifacts.

(3) Using a simple dimension reduction technique (i.e., principal component analysis [PCA]), the three main principal beats (corresponding to x, y, z dimensions) of the 12-lead ECG can be computed (FIG. 1, row 3). This technique accounts for differences in leads placement among patients.

(4) By filtering the T waves of PCA beats, the component coefficients of eigenvalues can be used to project the T loop into the x-y, x-z, or y-z dimensional planes (FIG. 1, row 4). Accordingly, novel markers of VRD can be computed from the main PCA beats and corresponding T loops.

Exemplary VRD Algorithms and VRD Components

VRD can be quantified, such as with a VRD score, using various qualities of the PCA of the 12-lead ECG, including any combination of the following:

(1) Temporal Qualities: As seen in FIG. 1, row 3, each eigenvalue of repolarization explains a percentage of variability in signal energy in that vector: a ratio between the second to first eigenvalues will yield a T wave complexity ratio, which is a global and robust measure of VRD. This ratio can be better visualized when the two main vectors are projected on x and y axes (FIG. 1, row 4). For example, in FIG. 1, Panel A, rows 3 and 4, the ratio is 0.09 (8%/89%), the corresponding loop shows more variability on the x versus the y axis and, hence, we see a thin loop. In FIG. 1, Panel B, rows 3 and 4, the ratio is 0.24 (18%/75%), the loop shows equal variability on both x and y axes and, hence, generates a fatter loop. Studies suggest that, in healthy hearts, the ratio should be less than 0.20. The non-dipolar T wave content measured beyond the third eigenvalue resembles T wave residua, another potential marker of VRD.

(2) Spatial Qualities: The energy signal propagation normally follows a homogenous pathway (FIG. 1, row 2), and the principal repolarization vector, or T wave axis, projects between 0° to 45° in the 3-D plane. The spatial T wave axis is a simple measure of global VRD. A more robust measure is the relevant deviation between the principal depolarization and repolarization vectors, or QRS-T angle. Given that both depolarization and repolarization signals follow the same propagation pathway, the deviation between both vectors should be ideally less than 100°. This angle is a sensitive measure of injury currents and VRD.

(3) Time Qualities: Ischemia simply alters the time the repolarization signal needs to travel through different regions of the myocardial wall. The J-T interval and Tpeak-Tend interval computed from the main PCA beat constitute the global (<250 milliseconds) and transmural (<100 milliseconds) repolarization times, respectively. These intervals are sensitive markers of VRD and can easily capture injury currents during phase 3 of the action potential.

(4) Other Qualities: T loop characteristics can resemble abnormalities in ventricular repolarization due to secondary electrical dispersion currents. These include T asymmetry (difference in slope profiles of ascending and descending loops), T notches (curvature of the loop), T flatness (kurtosis value of loop area), T loop area (3-Dimensional plane), proximal T loop width, and T loop morphology (area containing a part of the border of the corresponding T loop). Deviation degree between the differential planes of the QRS and T loops (total cosine R-to-T) also resembles global repolarization dispersion.

Figure 7A:
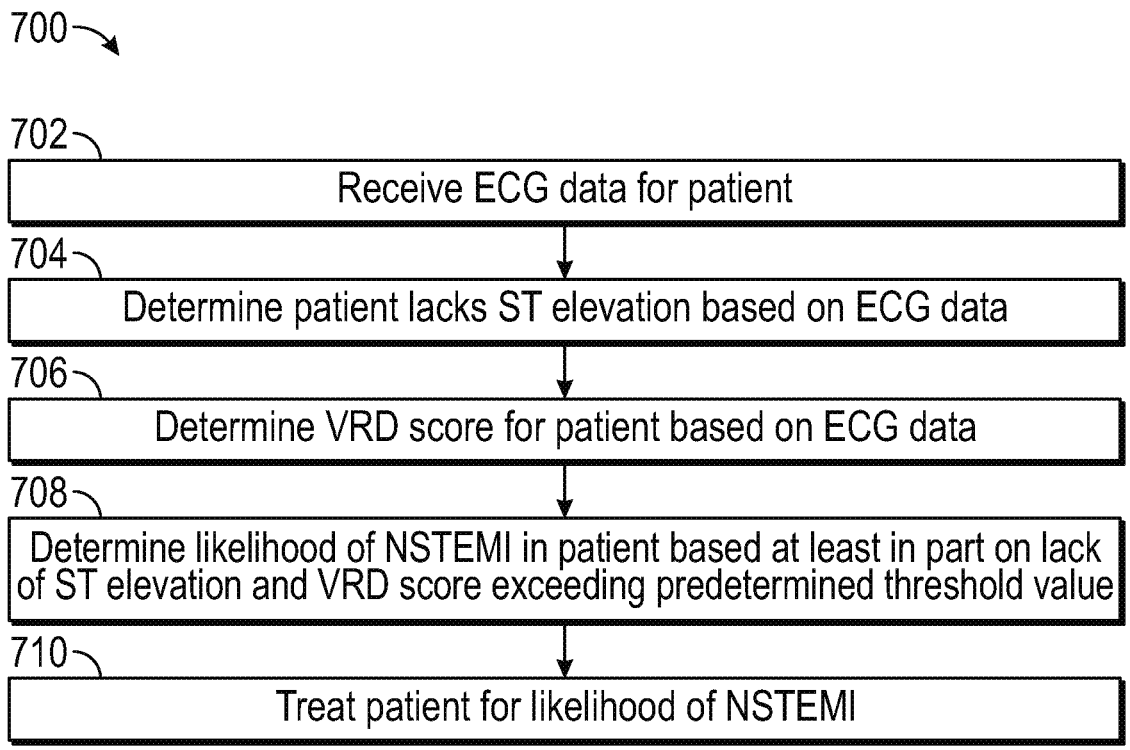
FIG. 7A is a flowchart illustrating an exemplary method of determining a likelihood of NSTEMI in a patient using ECG data.
Figure 7B:
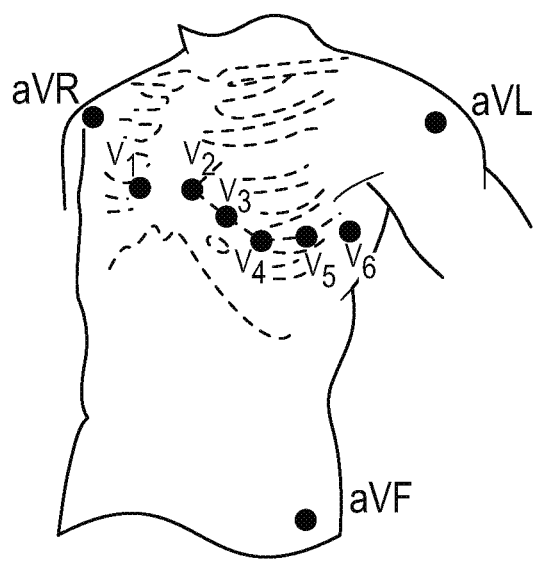
FIG. 7B shows certain exemplary ECG lead locations for a 12 lead ECG device.

FIG. 7 is a flow chart that illustrates an exemplary method for determining a likelihood of NSTEMI in a patient. At block 702, ECG data is received for a patient. The ECG data may be acquired using a 12-lead ECG system. At block 704, it is determined from the ECG data that the patient lacks ST elevation (STE). At block 706, a VRD score (determined using the T wave complexity ratio and/or other qualities of VRD described herein) for the patient is calculated using the ECG data. At block 708, a likelihood of NSTEMI in the patient is determined based at least in part on the lack of STE and a VRD score exceeding a predetermined threshold value. When a likelihood of NSTEMI is determined, the patient can then optionally be treated (block 710), such as by revascularization, stent placement, administering a thrombolytic therapy, or other appropriate treatments.

ECG files can be obtained for a patient in various forms, such as in binary XML signals. Such signals can be decompressed into common a data format (e.g., xls) in which the ECG leads can be decoded and stored in columnar matrices (e.g., 12 [leads]×5,000 [samples]). To control for baseline noise and artifacts, a baseline median beat can be computed for each ECG lead, which can yield a high signal-to-noise ratio and, hence, stable artifact-free averages. Using a simple dimension reduction technique (e.g., PCA), the main principal components of the 12 lead ECG can be computed. By filtering the STT waveforms of PCA components, the component coefficients of eigenvalues can be obtained, which can be used to project the spatial R and T loops. Accordingly, novel markers of VRD can be computed from the main PCA components and corresponding T loops.

Acute myocardial ischemia alters gap junction channel protein expression and, hence, leads to slow conduction and refractory action potential dispersion at ischemic fibers. The result is regional repolarization dispersion currents between various myocardial segments (e.g., endo-mid, endo-epi, apex-base, epi-mod, and/or endocardial walls), which indicates that early ischemic gradients that alter action potential amplitude, repolarization time, excitability, and conduction can contribute to various repolarization changes, other than STE, on the surface 12-lead ECT very early during MI evolution. Such ischemic injury is most likely to alter local gradients of repolarization manifested in the T waves prior to distorting the ST segment of the ECG. This can result in increased differences between STT waveforms of the 12-lead ECG. Isolating the principal repolarization components can identify the orthogonal vectors that contain the most significant information in the data, and can, therefore, provide means for evaluating ischemia-induced repolarization dispersion in the context of chest pain.

The following exemplary spatial and temporal T loop morphology descriptors can be used to differentiate a patient with NSTEMI from a non-ischemic patient, and thus can be used to determine a patient's VRD score:

(1) T wave complexity (TWC): defined as the average ratio of the second to first eigenvalues of repolarization. Larger values suggest more dispersed repolarization energy, which can indicate localized ischemic injury currents seen during myocardial infarction.

(2) T loop morphology dispersion (TMD): defined as a measure of the spatial T-wave morphology variation. Large values mean that the reconstructed vectors of different ECG leads are grossly different, which can indicate regional repolarization dispersion between ischemic and non-ischemic fibers.

(3) Total cosine R-to-T (TCRT): defined as the average of the cosines of the angles between T and R loops. Larger values mean greater vector deviation between depolarization and repolarization wavefront directions, which can indicate ischemia-induced repolarization dispersion.

Table 1 below provides additional information regarding these and several additional VRD metrics that can be used (in any combination) to determine a patient's VRD score and/or identify an increased likelihood of NSTEMI.

Disclosed methods can comprise identifying an increased likelihood of NSTEMI in a patient who lacks STE where the patient's VRD score exceeds a predetermined threshold value. The VRD score can be based on one or more of the spatial or temporal qualities of VRD for the patient described herein, including a T wave complexity ratio (TWC). The VRD score can also be based at least in part on the patient's TMD value and/or the patient's TCRT value. The predetermined threshold value for the VRD score can be any value that provides a meaningful indication of whether or not the patient is experiencing NSTEMI, such that VRD scores above the threshold value provide an actionable indication of an increased likelihood of NSTEMI in the patient. The value of the predetermined threshold value can be selected based on how great of a likelihood of NSTEMI is desired in a given situation. For example, VRD scores exceeding the threshold value can indicated that the patient should be provided a certain follow-up diagnostic procedure and/or an appropriate therapy to improve perfusion of myocardial tissue.

In some embodiments, machine learning (or other artificial intelligence) can be used to generate algorithms (e.g., a Bayes classification algorithm) to combine large amount of data (e.g., VRD metrics, demographics, and/or medical history) to compute the VRD scores or other values indicating probability or likelihood of NSTEMI. Bayes classifiers can be based on binary logistic regression, such that coefficients can be transformed logarithmically into binary outcomes (e.g., yes/no). In some embodiments, the VRD score can range from 0 to 1, with a higher value indicating a higher probability or likelihood of NSTEMI.

In some methods, the VRD score can be based solely on the T wave complexity ratio (TWC). In such methods, the predetermined threshold value for the VRD score can comprise a predetermined threshold value for TWC, such that TWC values equal to or greater than the predetermined threshold value for TWC indicate an increased likelihood of NSTEMI in a patient who lacks STE. In other methods, the VRD score can be based in part on TWC, such that the predetermined threshold value for the VRD score is based in part on a predetermined threshold value for TWC. For example, the predetermined threshold value for TWC can be at least at least 0.20, at least 22, at least 0.23, at least 0.24, at least 0.25, at least 0.26, at least 0.27, at least 0.30, at least 0.35, at least 0.40, at least 0.50, and/or at least 0.75 In some methods, the VRD score can be based at least in part on the T loop morphology dispersion (TMD) value. In such methods, the predetermined threshold value for the VRD score can be based on a predetermined threshold value for TMD, such that TMD values equal to or greater than the predetermined threshold value for TMD indicate an increased likelihood of NSTEMI in a patient who lacks STE. For example, the predetermined threshold value for TMD can be at least 30, at least 35, at least 40, at least 45, at least 50, and/or at least 55.

In some methods, the VRD score can be based at least in part on the total cosine R-to-T (TCRT) value. In such methods, the predetermined threshold value for the VRD score can be based on a predetermined threshold value for TCRT, such that TCRT values equal to or greater than the predetermined threshold value for TCRT indicate an increased likelihood of NSTEMI in a patient who lacks STE. For example, the predetermined threshold value for TCRT can be at least 0.20, at least 0.30, at least 0.40, at least 0.45, at least 0.50, at least 0.55, at least 0.60, and/or at least 0.65.

Table 1 below includes a several different VRD metrics that can be used in disclosed methods, systems, and devices. The table also provides exemplary definitions and computations for the different VRD metrics.

Statistical Analysis (1) Data Set Preparation. A final annotated dataset can be created using a MatLab program or similar program and can include prehospital clinical data elements (e.g., demographics, signs and symptoms, vital signs, medical history, and/or comorbidities), prehospital ECG metrics, and/or other data. The prehospital ECG metrics can include previously defined markers of VRD and common ECG metrics (e.g., RR

TABLE 1

| # | VRD Metric | | Exemplary Definition | Exemplary Computation |
|---|---|---|---|---|
| 1 | TWC-1 | T Wave Complexity | First to the sum of all PCA eigenvalues of the STT waveform | $PCA_1 = \dfrac{s_1}{\sqrt{\sum_{i=2}^{12} s_i^2}} \times 100$ |
| 2 | TWC-2 | | Second to first PCA eigenvalues of the STT waveform | PCA ratio 2 $PCA_2 = \dfrac{s_2}{s_1} \times 100$ |
| 3 | TWC-3 | | Third to first PCA eigenvalues of the STT waveform | PCA ratio 3 $PCA_3 = \dfrac{s_3}{s_1} \times 100$ |
| 4 | TWR | T Wave Residua | Sum of 4-8 eigenvalues of the STT waveform to all PCA eigenvalues | $\dfrac{\sum_{i=4}^{8} S_i}{\sum_{i=1}^{8} S_i} \times 100$ |
| 5 | T-AX | Spacial T axis | Spatial direction of the mean T vector in the 3D plane | |
| 6 | SQRSTA | Spacial QRS-T angle | Spatial angle between the mean T and R vectors in the 3D plane | |
| 7 | T-AS | T Asymmetry | Difference in slope profiles of ascending and descending loops | $\dfrac{\sum_{x=x_0}^{x_n} r(x)^2}{x_n - x_1}$ |
| 8 | T-NO | T Notches | Curvature of the loop | $ISRoC = \dfrac{\dfrac{\partial^2 y}{\partial x^2}}{\left[1 + \left(\dfrac{\partial y}{\partial x}\right)^2\right]^{3/2}}$ |
| 9 | T-FL | T Flatness | Kurtosis value of T loop area | $M_k = \left[\sum_{n=0}^{N-1} (n - M_1)^k \cdot V(n)\right]^{\frac{1}{k}}$ |
| 10 | TMD | T Loops Morphology Dispersion | Spatial variation of the reconstructed T vecotrs of different leads | $TMD = \dfrac{1}{21} \sum_{i,j \in \Gamma} \theta_{ij}$ where $\Gamma = \{I, II, V2, V3, V4, V5, V6\}$ |
| 11 | $TMD_{pre}$ | | TMD of the ascending loop of T wave | $(t_{TS} < t < t_{TP})$ |
| 12 | $TMD_{post}$ | | TMD of the descending loop of T wave | $(t_{TP} \leq t < t_{TE})$ |
| 13 | TCRT | Total Cosine-R-to-T | The wavefront direction between the R and T loops | $TCRT = \dfrac{1}{t'_{RE} - t'_{RS}} \int_{i=t'_{RS}}^{t'_{RE}} \cos(\angle(e_{T,1}, s_{QRS}(i)))$ |
| 14 | JTc | JT Interval | Total repolarization time (onset to offset of T wave) | |
| 15 | $T_{p-e}$ | Tpeak-Tend Interval | Transmural repolarization time (peak to offset of T wave) | | interval, QRS duration, QTc, and ST/T changes). A threshold for MI+ve event can be held as the primary classifier in the full dataset (e.g., n≈1,438), whereas threshold for MACE+ve can be held as the secondary classifier when an MI+ve event is detected (e.g., n≈259).

(2) Prediction Modeling Using Machine Learning. Machine learning can be used to identify, in real-time, (a) which chest pain patients seen during the prehospital context are having a coronary event, and then, if they are, (b) how likely it is that they will experience serious complications requiring aggressive therapy (e.g., translating into early administration of drugs, aggressive therapy, and close follow up). In a first stage, cases can be randomly assigned to either a training set or a testing set. This can include two steps: features selection and model learning. During features selection, the interactions of common ECG metrics and clinical characteristics—with the behavior/presence of VRD markers around defined MI+ve events—can be evaluated. This supervised learning process can identify statistically significant patterns of interactions (i.e., nodes) that might indicate clinically important events. During model learning, a maximum entropy classifier can model the probability of a chest pain case being in a particular class (MI+ve vs. MI−ve). This learning process can identify the optimal multivariate models utilizing the most relevant clinical and ECG metrics. The performance of different classification algorithms to assign accurate labeling (e.g., decisions) of the primary classifier can be evaluated in the testing set. The resulting algorithm/method can be refined to maintain a stable prediction power. Similar steps can be repeated among MI+ve cases to identify an optimal model to predict the probability of MACE+ve events. These methods can provide an artificial algorithm that can assign, in real-time, a probability score (i.e., low or high) of NSTEMI during the prehospital care of chest pain patients as well as a risk score (i.e., low or high) for those with high probability of NSTEMI.

(3) Deploying a Prototype Algorithm That Denotes Real-Time Probability of NSTEMI Events. In an exemplary study, a local three-hospital system was utilized, which was fully integrated with a prehospital division that commands all ambulances in the city of the hospitals. All prehospital ECGs were transmitted to a command center wherein disclosed algorithms were applied. The disclosed algorithms were linked to the command center, for example through an Internet computing cloud hosted on servers. All transmitted prehospital ECGs were then re-routed through disclosed algorithms so that the probability scores could be computed.

Baseline and Clinical Characteristics

Disclosed technology was used to transmit and acquire the requisite 12-lead ECGs from several EMS ambulances that transport patients to several local hospitals. This preliminary cohort contains the prehospital and inhospital clinical and ECG data of 600 chest pain patients (age 58±16 years, 56% males, 45% African-American) transported by EMS ambulances during a span of several months. Nearly 18% had acute MI (70% of them had NSTEMI), and of those 16% experienced 30-day death or re-infarction. Nearly 65% of those MI patients had initially negative troponins, and nearly 25% were admitted to non-PCI capable hospital. The disclosed algorithms has utilized this cohort as a training set to compute the necessary VRD markers to provide a real-time clinical decision support for early NSTEMI detection.

The Clinical Utility of T Wave Complexity

Figure 2:
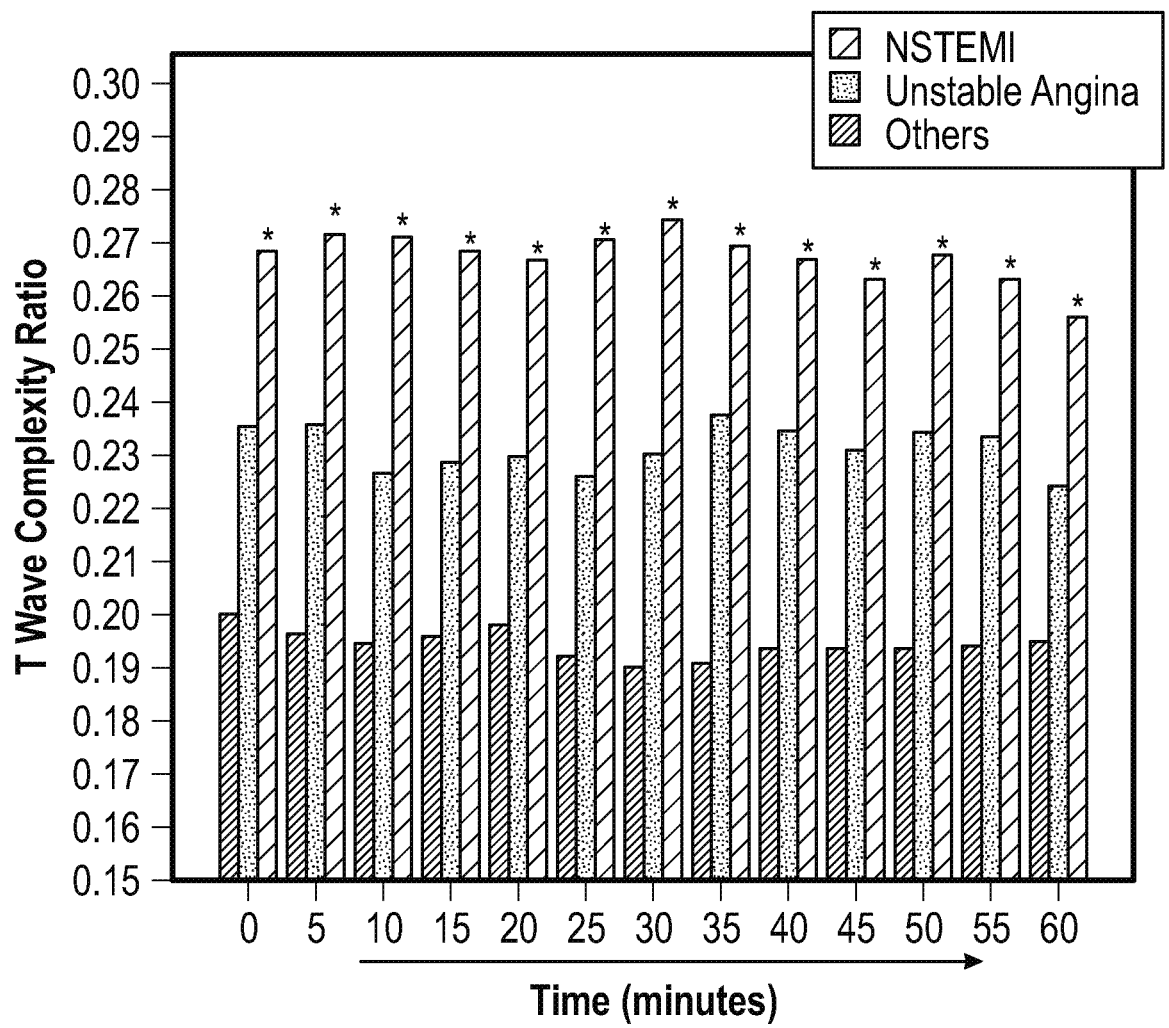
FIG. 2 illustrates the magnitude of VRD between groups (NSTEMI, unstable angina [ischemia but no injury], and others). This figure illustrates the mean repolarization complexity between groups. Time zero represents the baseline 12-lead ECG, and other time points represent the 5-minute averages. (*) denotes significant against "others" subcategory using RM-ANOVA with Tukey's post hoc adjustment.
Figure 3A:
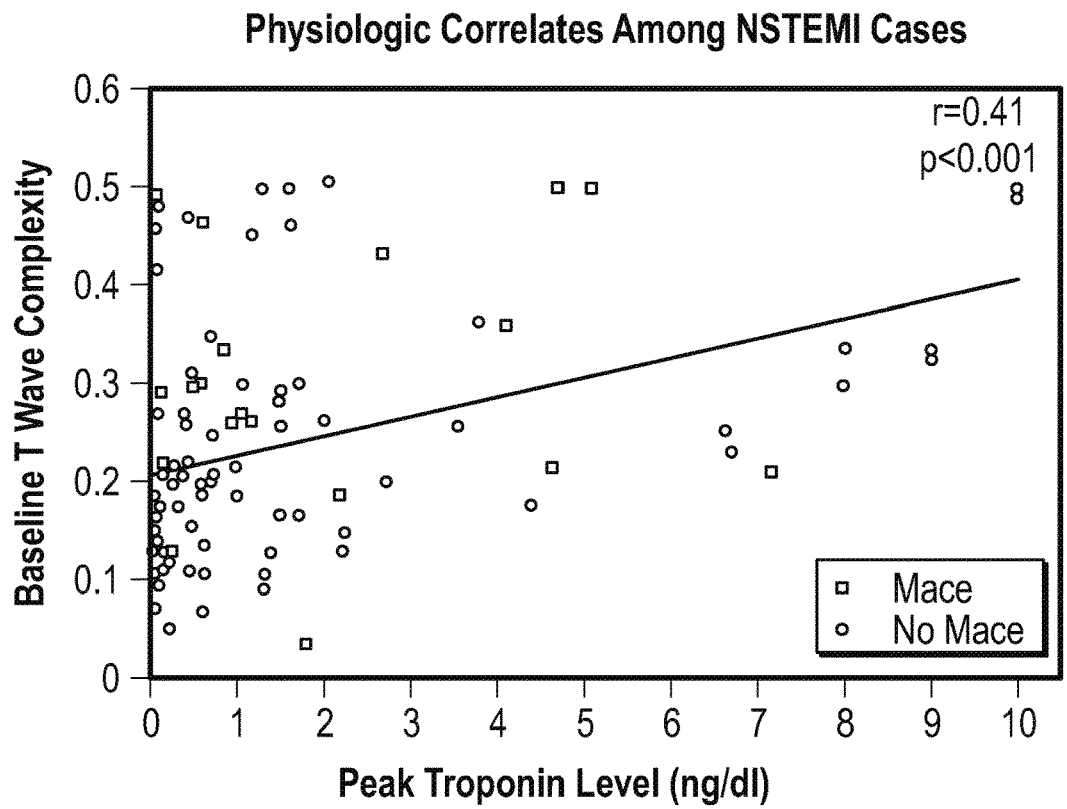
FIGS. 3A and 3B illustrate physiologic correlates and classification performance of VRD.
Figure 3B:
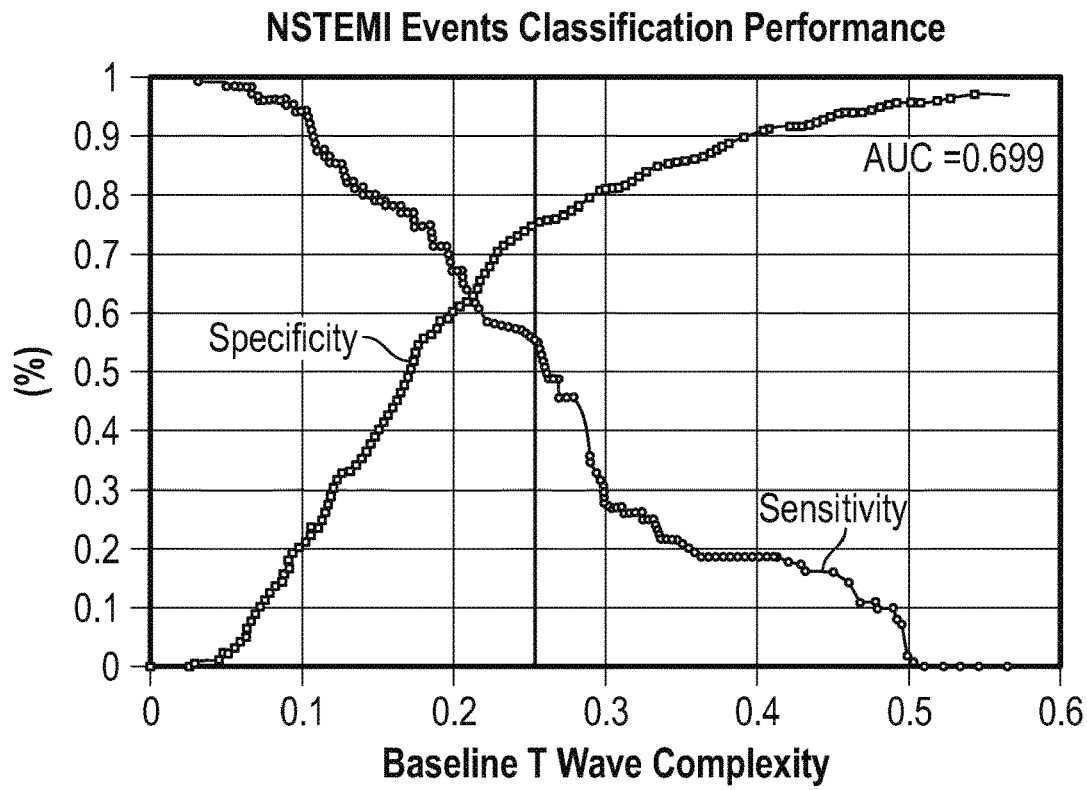
Figure 4:
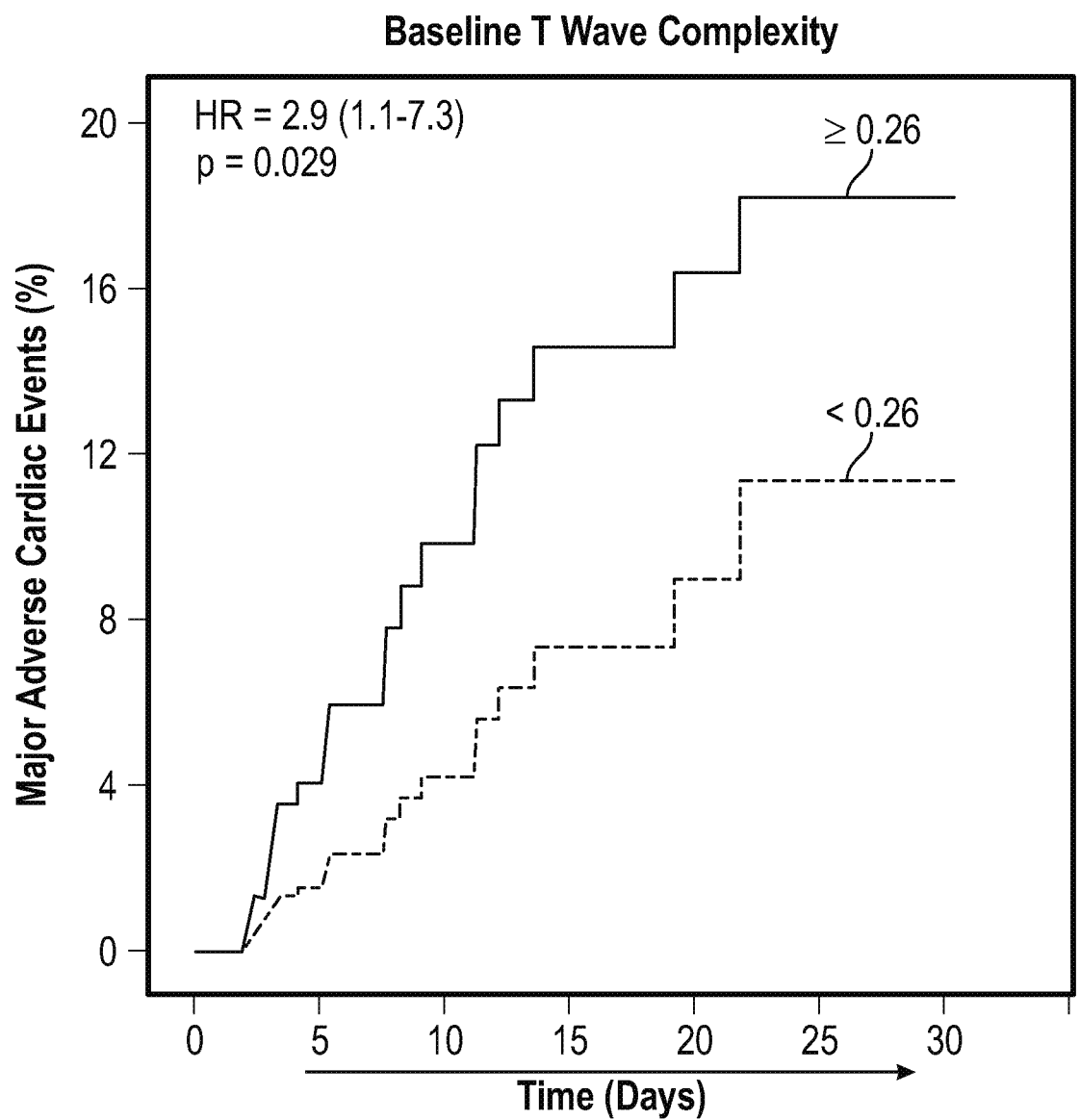
FIG. 4 shows Kaplan-Meier events probability curves for in-hospital MACE. This figure compares time-to-MACE between those with T wave complexity below 0.26 (n=250) and above or equal to 0.26 (n=119).

The baseline T wave complexity ratio demonstrated greater VRD among NSTEMI subjects compared to all other subjects and this differential power was maintained throughout the initial 60-minute of ECG recording in the ED (FIG. 2). Of note, measures of VRD can differentiate NSTEMI from others without coronary events, but may be less effect at differentiating UA, indicating that measures of VRD can be more sensitive to myocardial injury than myocardial ischemia. This finding is significant given that UA currently constitutes a clinical challenge, and being able to isolate NSTEMI patients early during triage can help improve outcomes in this subcategory. Moreover, the baseline T wave complexity ratio was positively correlated with peak troponin level (r=0.41, p<0.001, FIG. 3A) and the total area under the curve (AUC) for the T wave complexity ratio as a classifier of NSTEMI events was 70% (FIG. 3B). This important correlation again supports a role for VRD in ischemic injury detection and suggests that the larger the ischemic damage in the myocardium the greater is the VRD. This finding indicates that measures of VRD can quantify myocardial ischemic burden in the absence of STE.

Disclosed studies demonstrate that indices of VRD on baseline 12-lead ECG not only can differentiate NSTEMI patients from UA and other non-ischemic chest pain patients very early during evaluation, but also correlate with the risk of adverse in-hospital outcomes. This is the first known study to test the clinical utility of VRD indices to detect and risk-stratify NSTEMI patients in the ED. The findings support the notion that endo-mid-mural ischemia, associated with ruptured plaques and partial coronary artery occlusion, can precipitate quantifiable T wave distortions prior to any ST segment displacement. This makes sense because ischemic injury is most likely to alter local gradients of repolarization manifested in the T waves (i.e., phase 3 of the action potentials) prior to distorting the ST segment (i.e., phase 2 and 3 of the action potentials) of the ECG. As such, test data suggests that, compared to ST segment deviation, a measure of global VRD is not only more sensitive, but also still specific enough for (1) detecting ischemic myocardial necrosis associated with endo-mid-mural ischemia in NSTEMI and (2) quantifying the severity of ischemic burden to identify high-risk NSTEMI patients who would benefit from early revascularization.

VRD and Ischemic Myocardial Injury

Myocardial ischemia induces electrophysiological alterations in action potentials, causing repolarization dispersion between normal and ischemic fibers and between epicardium and endocardium, which can be detected on the surface 12-lead ECG. However, despite the ongoing electrical dispersion currents during ischemic injury, STE only evolves when action potential differences in epicardial and endocardial cells drop to below 65 mV. This indicates that early transmural gradients in action potential amplitude, repolarization time, excitability, and conduction contribute to various VRD changes—other than STE—on the surface 12-lead ECG very early during MI evolution (i.e., myocardial injury). Test results are congruent with these findings and show that T wave complexity ratio demonstrates greater VRD among NSTEMI (i.e., myocardial injury), but not UA (i.e., ischemia), when compared to all other chest pain subjects.

To date, current guidelines do not precisely describe the evolution of ischemic ECG changes associated with NSTEMI, and there is a lack of clinical studies on the topic. It has been shown that ST depression—in conjunction with T wave inversion—in NSTEMI correlates with significant left main coronary disease and subsequent MACE. In studies, these changes had poor sensitivity to detect myocardial injury and were not predictive of MACE. On the contrary, human data from experimental models supports the finding that ischemic injury leads to VRD.

In an experiment that examined the evolution of different temporal and spatial VRD indices during artificially-induced transmural ischemia in 95 patients undergoing PCI, dynamic ECG changes were recorded during and after 5-minute balloon inflation in each of the dominant coronary arteries. Repolarization time and complexity were found to change significantly within 2 minutes following balloon inflation (and disappear immediately following balloon deflation), which indicates the transient nature of such changes. These findings demonstrate that VRD changes persist in NSTEMI patients over longer periods, such as throughout the initial 60 minutes of ED admission, when patients are usually waiting for cardiac enzyme results. This is a time window in which treatments to restore coronary perfusion might be administered to those at greater risk of adverse events. There is an opportunity for this change in approach, given that only 25% of those with increased repolarization complexity in this study were treated by PCI.

In test data, overall repolarization complexity is higher (22% vs 11%) compared to other general populations, which may be because nearly 65% of the sample had some degree of cardiovascular disease. This would be reasonable given that other physiological (e.g., CAD) and psychological (e.g., depression) factors besides ischemia can induce non-specific ST-T changes. However, despite the non-specific repolarization changes seen in the sample at baseline, myocardial ischemia resulted in clear increases in the T wave complexity ratio between groups for more than 60 minutes, confirming that ischemia-induced changes in VRD are significantly greater than other non-specific factors in the context of chest pain.

Nevertheless, test data shows a simple linear relationship between magnitude of VRD and peak troponin levels. In addition to a correlation (e.g., $R^2=17\%$), there is also a logical association between magnitude of VRD and degree of ischemic myocardial necrosis. Along with multiple other potential factors, this can explain the ability of T wave complexity to identify in-hospital MACE in our data.

Clinical Implications

Figure 5A:
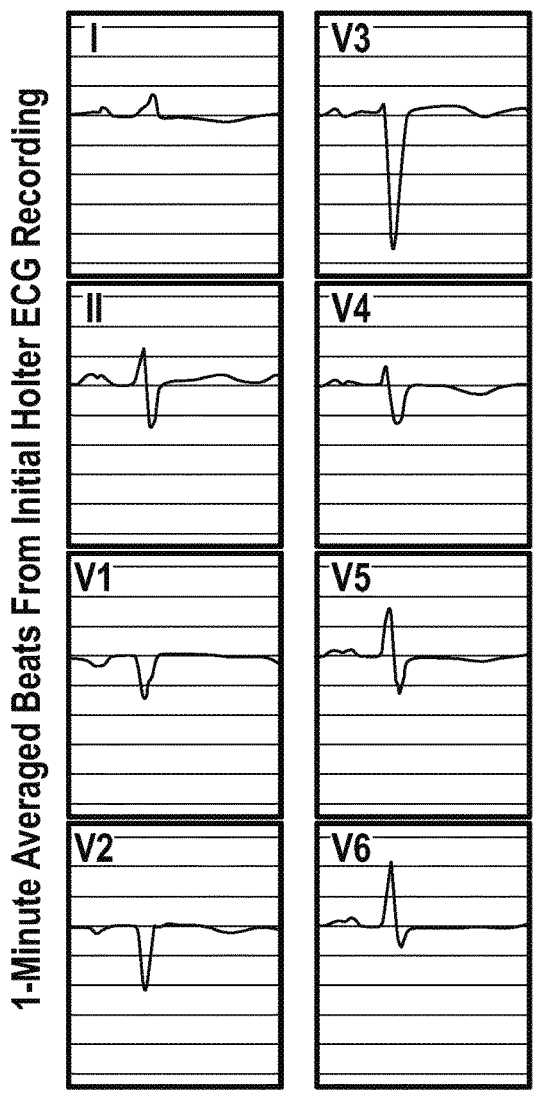
FIGS. 5A and 5B illustrate baseline ECG (FIG. 5A) and corresponding VRD trend (FIG. 5B) in an exemplary patient: a case of a 70 year-old female with no prior history of CAD, HTN, or DM. Initial troponin was 10.4 ng/dl but there was no significant ST changes on admission ECG. She experienced non-sustained ventricular tachycardia and was sent to the catheterization lab four hours after her initial presentation. Angiography revealed 95%, 80%, and 30% occlusions in the LAD, LCx, and RCA coronary arteries.
Figure 5B:
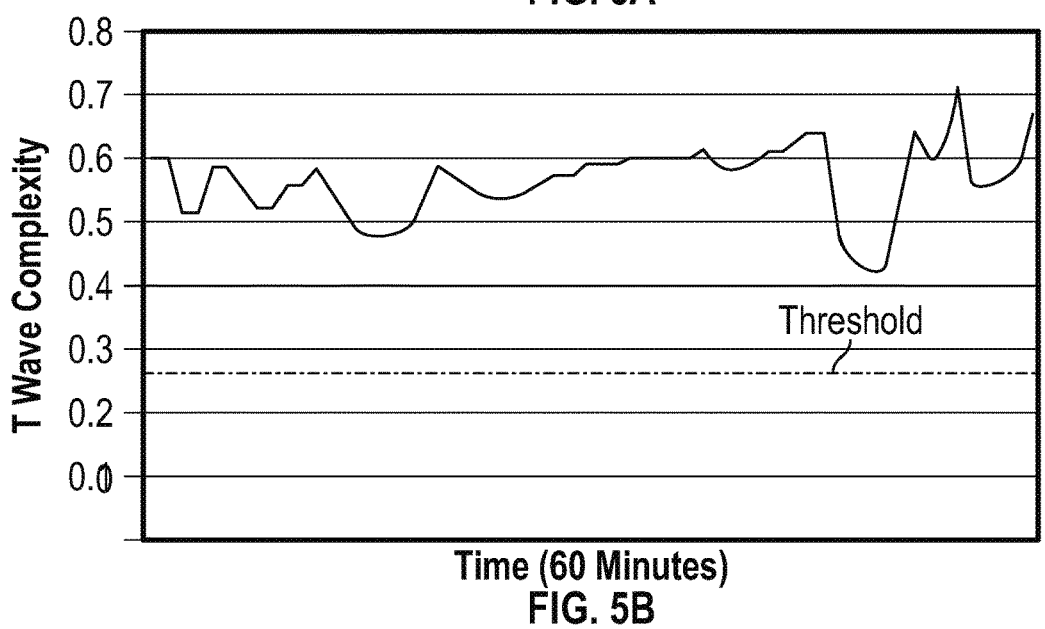
Figure 6:
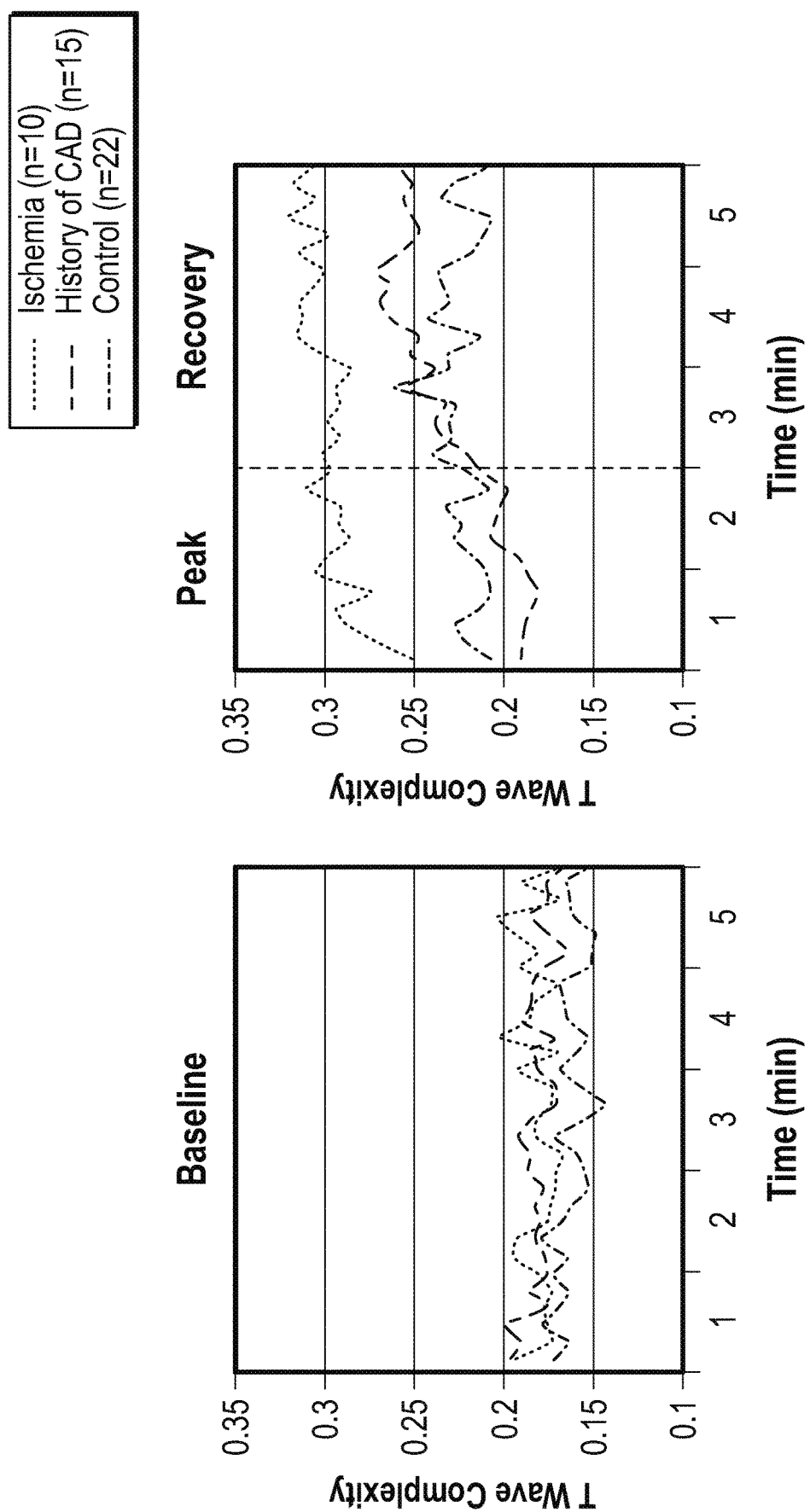
FIG. 6 shows changes in T Wave Complexity over time for pateints during exercise testing. "Baseline" denotes baseline prior to exercise, "Peak" denotes changes at peak of the exercise test (where most ischemic changes occur), and "Recovery" denotes recovery after stopping the test.

The flow of electrical currents across the boundaries between the ischemic and non-ischemic zones (i.e., injury currents, see FIG. 1, Panel B, row 2) precipitates changes in repolarization time, excitability, and conduction in most patients with acute coronary events. Test data indicates that markers of VRD are sensitive to such ischemic repolarization changes (phase 3 action potential), which explains why STE only evolves during severe transmural ischemia that alters phase 2 of action potential as well. For example, FIGS. 5A and 5B illustrate a case of a 70 year-old Caucasian female with no known CAD who had no ST changes on the presenting ECG. However, due to recurrent angina that precipitated transient ventricular arrhythmia, she underwent PCI (door-to-balloon time=4 hours) that showed 95% occlusion in the proximal LAD. These findings logically support the notion that distortion of the T wave occurs prior to any ST-segment displacement (i.e., more sensitive to non-transmural myocardial injury), indicating that VRD plays a significant role in detecting acute coronary events in chest pain patients.

The issue of NSTEMI detection is complex. In contrast to STEMI, in which most patients have ongoing ischemia, in NSTEMI there are fluctuations. Actually a large part of these patients present after resolution of symptoms and ECGs are recorded when the patient does not have active ischemia, which might justify the moderate sensitivity (57%) of T wave complexity reported in this study. To make things even more complicated, a patient may be seen during a short episode of ischemia that does not result in leak of troponin. This is demonstrated in our data where T wave complexity correlates with myocardial injury (i.e., NSTEMI) and not myocardial ischemia alone (i.e., UA), which explains the relatively stable trends in T wave complexity during initial ED presentation (FIG. 2). Finally, it has been demonstrated that continuous ECG recording, especially when there are fluctuations in the patient's symptoms, may detect subtle changes that otherwise could be overlooked. Test data supports these recommendations and suggest that performing continuous ECG monitoring (~60-min) can help rule out low-risk patients with a negative predictive value up to 84%.

Exemplary methods can include determining that a patient has a high likelihood of NSTEMI, based on the methods disclosed herein, and then treating the patient accordingly. Patients can be treated with various therapies that improve or restore perfusion to the myocardial tissue. For example, such therapies can include performing coronary artery angioplasty in the patient, stent placement, and/or administering a thrombolytic therapy to the patient. Exemplary thrombolytic therapies can include drugs such as tPAs, Lanoteplase, Reteplase, Staphylokinase, Streptokinase (SK), Tenecteplase, and Urokinase.

Exemplary Implementation of Disclosed Technology with Patient ECG Data

Figure 8:
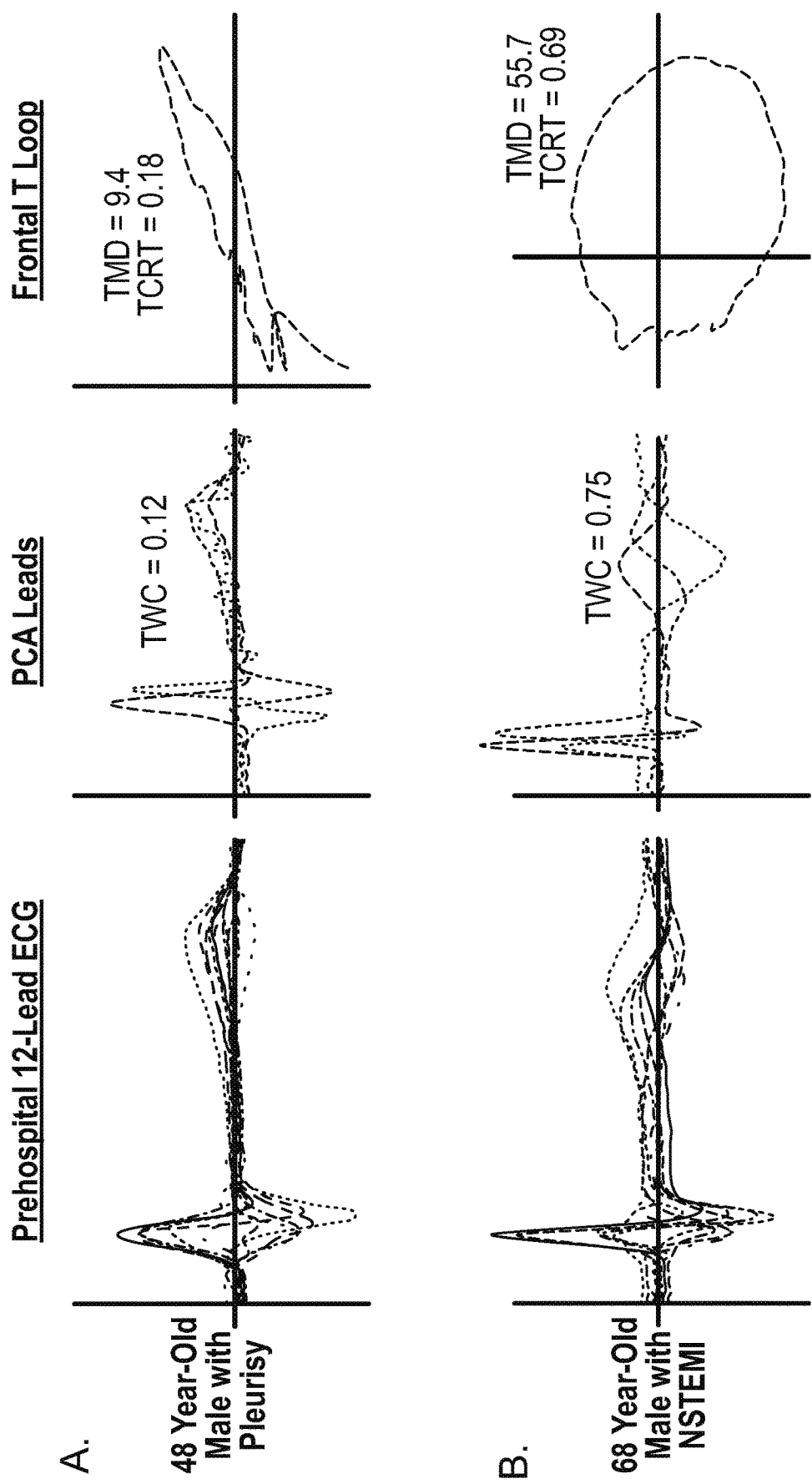
FIG. 8 illustrates exemplary principal component analyses of 12 lead ECGs for two patients. Despite the nonspecific T wave changes seen in both patients, the applied PCA technique reveals greater STT morphology deviation between main PCA components and a subsequently broader T loop for the ischemic patient (row B) compared to the non-ischemic patient (row A), indicating an increased likelihood of NSTEMI.

FIG. 8 illustrates exemplary principal component analyses of the 12-lead ECG signals for two patients seen in a clinical setting. Row A is for a 48 year-old male (patient A) with pleurisy, and row B is for a 68 year-old male (patient B) with NSTEMI. Both patients presented with non-traumatic, substernal chest pain, had no prior history of hypertension, diabetes, CAD, or smoking, and had non-specific T wave changes but negative cardiac troponin values upon admission. Accordingly, both patients were triaged and managed the same. However, the patient B became hemodynamically unstable with a sudden rise in serum troponin and was consequently sent for angiography, which revealed 90% occlusion of the left anterior descending artery, requiring stent placement. In FIG. 8, the first column shows the prehospital ECG data for each patient, the second columns shows the PCA leads data for each patient along with the corresponding TWC values, and the third column shows the frontal T loops for each patient along with their corresponding TMD and TCRT values. Patient A had a low TWC value of 0.12, whereas patient B had a much higher TWC value of 0.75, indicating a significantly higher likelihood of NSTEMI in patient B. Similarly, patient A had a low TMD value of 9.4 and a low TCRT value of 0.18, whereas patient B had a much higher TMD value of 9.4 and a much higher TCRT value of 0.69, also indicating a significantly higher likelihood of NSTEMI in patient B.

As shown in FIG. 8, despite the non-specific T wave changes seen in both patients, the disclosed PCA technique reveals greater STT morphology deviation between main PCA components and a subsequently broader T loop (e.g., the T loop had a greater maximum width along the vertical PCA-2 axis, and/or a greater total area within the T loop) for the ischemic patient B compared to the non-ischemic patient A. Accordingly, application of the disclosed technology to the ECG data of patients A and B could have been used to more accurately and quickly diagnose and differentiate the two patients' conditions, and accordingly could have led to much quicker discovery of patient B's artery occlusion and subsequent treatment.

Exemplary 12-Lead ECG Devices and Applications

Conventional 12-lead ECG devices include ten electrodes that are placed on a patient's limbs and chest. The overall magnitude of the heart's electrical potential is then measured from twelve different angles or "leads" using the ten electrodes, and the ECG data is recorded over a period of time (such as 10 seconds). In this way, the overall magnitude and direction of the heart's electrical depolarization is captured at each moment throughout the cardiac cycle. Exemplary 12-lead ECG devices that are commercially available include the "Burdick ELI 230" 12-lead interpretive resting ECG device available from Mortara Instrument, and the "MAC 1200" 12-channel ECG device available from GE Healthcare. The ten electrodes of a 12-lead ECG device can be placed at ten different locations on a patient's body. For example, the ten locations can include the following ten locations:

RA On the right arm.
LA In the same location where RA is placed, but on the left arm.
RL On the right leg, lateral calf muscle.
LL In the same location where RL is placed, but on the left leg.
V1 In the fourth intercostal space just to the right of the sternum.
V2 In the fourth intercostal space just to the left of the sternum.
V3 Between leads V2 and V4.
V4 In the fifth intercostal space in the mid-clavicular line.
V5 Horizontally even with V4, in the left anterior axillary line.
V6 Horizontally even with V4 and V5 in the midaxillary line.

The term "lead" in ECG refers to 12 different vectors along which the heart's depolarization is measured and recorded. There are a total of six limb leads and augmented limb leads arranged like spokes of a wheel in the coronal plane and six precordial leads that lie on the perpendicular transverse plane. In medical settings, the term "leads" is also used to refer to the ten electrodes themselves. Each of the 12 leads represents the electrical potential difference between two points. For each lead, the positive pole is one of the ten electrodes. In bipolar leads, the negative pole is a different one of the electrodes, while in unipolar leads, the negative pole is a composite pole known as Wilson's central terminal. Wilson's central terminal Vw is produced by averaging the measurements from the electrodes RA, LA, and LL to give an average potential across the body.

The 12 leads can include three limb leads: lead I, lead II, and lead III, three augmented limb leads: augmented vector right (aVR), augmented vector left (aVL), and augmented vector foot (aVF), and six precordial leads ($V_1$-$V_6$). Lead I is the voltage between the (positive) left arm (LA) electrode and right arm (RA) electrode. Lead II is the voltage between the (positive) left leg (LL) electrode and the right arm (RA) electrode. Lead III is the voltage between the (positive) left leg (LL) electrode and the left arm (LA) electrode. Lead aVR has the positive electrode on the right arm, and the negative pole is a combination of the left arm electrode and the left leg electrode. Lead aVL has the positive electrode on the left arm, and the negative pole is a combination of the right arm electrode and the left leg electrode. Lead aVF has the positive electrode on the left leg, and the negative pole is a combination of the right arm electrode and the left arm electrode. The six precordial electrodes ($V_1$-$V_6$) act as the positive poles for the six corresponding precordial leads (V1-V6), with Wilson's central terminal used as the negative pole.

FIG. 7A illustrates locations for electrodes V1-V6, corresponding to precordial leads $V_1$-$V_6$, along with representations of the three augmented limb leads aVR, aVL, and aVF.

The 12-lead ECG device can comprise, or be part of a ECG system that further comprises, signal receiving and processing devices, other computing hardware such as a processor and memory, displays, user interfaces, data transmission devices, etc., as discussed further below. Such a device or system can be used to implements the methods disclosed herein.

More information regarding ECG methods, systems, and devices can be found in International Application No. PCT/US2016/025333, filed on Mar. 31, 2016, which is incorporated by reference herein in its entirety.

Exemplary Computing Environments and Implementations

Any of the disclosed methods can be implemented using computing hardware and/or as computer-executable instructions stored on one or more computer-readable storage devices (e.g., one or more optical media discs, volatile memory components (such as DRAM or SRAM), or non-volatile memory components (such as flash memory or hard drives)) and executed on a computer (e.g., any commercially available computer, including smart phones or other mobile devices that include computing hardware). The term computer-readable storage device does not include communication connections, such as signals and carrier waves. Any of the computer-executable instructions for implementing the disclosed techniques as well as any data created and used during implementation of the disclosed embodiments can be stored on one or more computer-readable storage device. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of software-based implementations of the disclosed methods are described. Other details that are well known in the art are omitted. For example, the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware.

Any methods or functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The innovations disclosed herein may be implemented in diverse general-purpose or special-purpose computing systems. Exemplary suitable computing environments in which the described innovations may be implemented can comprise any of a variety of computing devices (e.g., desktop computer, laptop computer, server computer, tablet computer, media player, gaming system, mobile device, etc.). For example, the computing environment can include one or more processing units and memory. The processing units can execute computer-executable instructions. A processing unit can be a general-purpose central processing unit (CPU), processor in an application-specific integrated circuit (ASIC) or any other type of processor. The system can include tangible memory, such as volatile memory (e.g., registers, cache, RAM), non-volatile memory (e.g., ROM, EEPROM, flash memory, etc.), or some combination of the two, accessible by the processing unit(s). The memory can store software for implementing one or more methods described herein, in the form of computer-executable instructions suitable for execution by the processing unit(s).

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Any of the features or characteristics described herein in relation to any one or more of the described embodiments can also be used with or included in any of the other described embodiments where possible, even if such features or technologies are not specifically mentioned in direct connection to a specific embodiment.

Characteristics, materials, numerical values, and other features described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims.

The invention claimed is:

1. An electrocardiographic (ECG) method for detecting non-ST elevation myocardial infarction (NSTEMI) from ECG data, implemented using computing hardware, the method comprising:
   receiving ECG data for a patient acquired via an ECG acquisition machine;
   determining, by computing hardware, that the patient lacks ST elevation (STE) based on the ECG data;
   determining, by computing hardware, one or more spatial or temporal qualities of ventricular repolarization dispersion (VRD) from the ECG data for the patient, the one or more spatial or temporal qualities of VRD including a T wave complexity ratio;
   determining, by computing hardware, a VRD score for the patient based on the one or more spatial or temporal qualities of VRD; and
   identifying an increased likelihood of NSTEMI in the patient who lacks STE where the VRD score exceeds a predetermined threshold value.

2. The method of claim 1, further comprising:
   treating the patient identified to have an increased likelihood of NSTEMI with a therapy to improve perfusion of myocardial tissue.

3. The method of claim 1, wherein the T wave complexity ratio is a ratio of second and first eigenvalues of repolarization, wherein the second and first eigenvalues of repolarization are derived from the ECG data for the patient.

4. The method of claim 1, wherein determining the VRD score comprises filtering T waves of the ECG data to derive main principal components analysis (PCA) beats from the ECG data.

5. The method of claim 4, wherein deriving main principal components analysis (PCA) beats comprises reducing the ECG data into three principal beats corresponding to first, second, and third eigenvalues of repolarization.

6. The method of claim 1, wherein receiving ECG data for the patient comprises acquiring the ECG using a 12-lead ECG device or system.

7. The method of claim 1, wherein the ECG data is acquired from the patient when the patient does not have active ischemia but does have myocardial infarction (MI).

8. The method of claim 1, further comprising determining a likelihood of a major adverse cardiac event (MACE) in the patient based on the determination of a likelihood of NSTEMI in the patient.

9. The method of claim 2, wherein treating the patient with a therapy to improve perfusion of myocardial tissue comprises performing coronary artery angioplasty in the patient.

10. The method of claim 2, wherein treating the patient with a therapy to improve perfusion of myocardial tissue comprises administering a thrombolytic therapy to the patient.

11. A computing device configured to perform the method of claim 1.

12. A computer-readable storage device storing computer-readable instructions for executing the method of claim 1.

13. The method of claim 1, wherein the one or more spatial or temporal qualities of VRD comprises T loop morphology dispersion (TMD).

14. The method of claim 1, wherein the one or more spatial or temporal qualities of VRD comprises total cosine R-to-T (TCRT).

15. An electrocardiographic (ECG) system comprising:
an ECG measurement device configured to acquire ECG signals from a person, the ECG measurement device comprising a plurality of electrodes configured to be brought into contact with the person's body to measure ECG signals from the person's body;
processing hardware coupled to the electrodes and configured to generated ECG data for the person from the measured ECG signals; and
computing hardware configured to:
determine that the patient lacks ST elevation (STE) based on the ECG data;
determine a ventricular repolarization dispersion (VRD) score for the person based on the ECG data, the VRD score being based on temporal or spatial qualities of repolarization derived from the ECG data; and
identify an increased likelihood of NSTEMI in the person based on the lack STE and based on the VRD score exceeding a predetermined threshold value.

16. The system of claim 15, wherein the VRD score is determined based on principal component analysis (PCA) for computing eigenvalues of repolarization.

17. The system of claim 15, wherein the computing hardware is configured to filter T waves of the ECG data to derive main PCA beats from the ECG data.

18. The system of claim 15, wherein the computing hardware is configured to reduce the ECG data into three principal beats corresponding to first, second, and third eigenvalues of repolarization.

19. The system of claim 15, wherein the computing hardware is also configured to determine a likelihood of a major adverse cardiac event (MACE) in the patient based on the determination of a likelihood of NSTEMI in the person.

20. The system of claim 15, wherein the ECG measurement device comprises a 12-lead ECG acquisition device.

21. A method for treating a patient for a heart condition, the method comprising:
identifying a patient with a likelihood of non-ST elevation myocardial infarction (NSTEMI) using ECG data for the patient by:
determining that the patient lacks ST elevation (STE) based on the ECG data;
determining one or more spatial or temporal qualities of ventricular repolarization dispersion (VRD) from the ECG data for the patient, the one or more spatial or temporal qualities of VRD including a T wave complexity ratio;
determining a VRD score for the patient based on the one or more spatial or temporal qualities of VRD; and
identifying an increased likelihood of NSTEMI in the patient who lacks STE where the VRD score exceeds a predetermined threshold value; and
performing a reperfusion therapy on the identified patient.

22. An electrocardiographic (ECG) method comprising:
receiving ECG data related to a person;
determining that the person lacks ST elevation (STE) based on the ECG data;
determining one or more spatial or temporal qualities of ventricular repolarization dispersion (VRD) from the ECG data for the person, the one or more spatial or temporal qualities of VRD including a T wave complexity ratio;
determining a VRD score for the person based on the one or more spatial or temporal qualities of VRD; and
determining that the VRD score exceeds a predetermined threshold value.

23. The method of claim 22, wherein receiving ECG data related to the person comprises applying ECG electrodes to the patient and detecting ECG signals from the person via the electrodes.

* * * * *

UNITED STATES PATENT AND TRADEMARK OFFICE
CERTIFICATE OF CORRECTION

PATENT NO. : 10,820,822 B2
APPLICATION NO. : 15/562196
DATED : November 3, 2020
INVENTOR(S) : Salah Al-Zaiti Page 1 of 1

It is certified that error appears in the above-identified patent and that said Letters Patent is hereby corrected as shown below:

In the Claims

Column 19, Line 18, Claim 15, "to generated ECG data" should read -to generate ECG data- Column 19, Line 29, Claim 15, "on the lack STE" should read -on the lack of STE- Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*